United States Patent
Laiosa (10) Patent No.: US 10,426,897 B2
(45) Date of Patent: Oct. 1, 2019

(54) CONTAINER HOLDER ASSEMBLY FOR A MEDICAMENT DELIVERY DEVICE AND MEDICAMENT DELIVERY DEVICE COMPRISING THE CONTAINER HOLDER ASSEMBLY

(71) Applicant: SHL Carebay Europe Ltd., Sliema (MT)

(72) Inventor: John Laiosa, Lodi, CA (US)

(73) Assignee: Carebay Europe LTD, Sliema (MT)

( * ) Notice: Subject to any disclaimer, the term of this patent is extended or adjusted under 35 U.S.C. 154(b) by 473 days.

(21) Appl. No.: 15/141,227

(22) Filed: Apr. 28, 2016

(65) Prior Publication Data
US 2017/0312451 A1 Nov. 2, 2017

(51) Int. Cl.
*A61M 5/32* (2006.01)
*A61M 5/20* (2006.01)

(52) U.S. Cl.
CPC ........ *A61M 5/3204* (2013.01); *A61M 5/2033* (2013.01); *A61M 5/2053* (2013.01); *A61M 5/3243* (2013.01); *A61M 2005/206* (2013.01); *A61M 2005/208* (2013.01)

(58) Field of Classification Search
CPC .............. A61M 5/3204; A61M 5/2033; A61M 2005/208; A61M 2005/206; A61M 5/2053; A61M 5/3243
See application file for complete search history.

(56) References Cited

U.S. PATENT DOCUMENTS

| 10,058,654 B2 | 8/2018 | Gabrielsson |
| 2014/0257193 A1* | 9/2014 | Bostrom ............. A61M 5/2033 604/197 |
| 2014/0336589 A1* | 11/2014 | Sund ................... A61M 5/2033 604/198 |
| 2015/0203186 A1 | 7/2015 | Lunney et al. |
| 2014/0036589 A1 | 2/2017 | Parthasarathy et al. |

FOREIGN PATENT DOCUMENTS

| TW | 201529115 A | 8/2015 |
| WO | 2011040861 A1 | 4/2011 |
| WO | 2015018578 A1 | 2/2015 |

OTHER PUBLICATIONS

Notification of Transmittal of The International Search Report and The Written Opinion of the International Searching Authority, or the Declaration issued in the International Application No. PCT/EP2017/058308 dated Jul. 17, 2017.
Search Report issued in Taiwanese Patent Application No. 106112621 dated Nov. 29, 2017.

* cited by examiner

*Primary Examiner* — Lauren P Farrar
(74) *Attorney, Agent, or Firm* — McDonnell Boehnen Hulbert & Berghoff LLP (57) ABSTRACT

Container holder assembly for a medicament delivery device comprising a housing part 22, a container holder 50, and a spring-biased needle guard 82, wherein the needle guard 82 is configured to disconnect from the container holder 50 upon movement from the extended position to the retracted position.

21 Claims, 7 Drawing Sheets

CONTAINER HOLDER ASSEMBLY FOR A MEDICAMENT DELIVERY DEVICE AND MEDICAMENT DELIVERY DEVICE COMPRISING THE CONTAINER HOLDER ASSEMBLY

TECHNICAL FIELD

The present invention relates to a container holder assembly for a medicament delivery device and in particular to a container holder assembly in which an actuator is releasably connected to a container holder.

BACKGROUND

There are numerous devices for delivering medicament on the market where the medicament is arranged in a container, such as a syringe, a cartridge or the like, and wherein the medicament is ejected through a delivery member, such as a needle or a nozzle, by having a movable stopper, inside the container, exert a pressure on medicament via a spring-biased drive member, which acts on the stopper.

A group of medicament delivery devices are defined as auto-injectors, wherein at least one of the steps of a delivery sequence is performed automatically, through a spring-biased mechanism, as a consequence of the user pressing a button or as a consequence of a previous mechanism reaching a certain stage. The steps that may be automatically activated are normally skin penetration by the delivery member, e.g. a needle, medicament delivery, and/or delivery member retraction.

In the case of automatic delivery of a medicament, a drive member, such as a plunger rod, often needs to be spring-biased, but prevented from moving until the appropriate moment. In some cases the user may determine when it is time to administrate the medicament. In other cases the medicament may be delivered when the needle has reached a certain depth after penetrating the skin. In the latter case, to initiate the automatic sequence, an actuator needs to be triggered by a user of the delivery device. The actuator may in some cases be button to be pressed by the user. The actuator may also be a movable element which triggers the automatic sequence as the delivery device is applied to the delivery site and moved in relation to the site.

It is also important to prevent the various components from moving in relation to each other during transport and handling of the medicament delivery device, i.e. during non-medical handling of the device. Depending on the different types of mechanisms for penetration, injection and possibly withdrawal, safety measures that do not interfere with the normal functions of the device need to be introduced. It may, for instance, be necessary to keep a movable container holder and medicament container from moving until it the device is unlocked. Such movement prevention means may be separated from activation prevention means but they may still need to be unlocked during an activation sequence when the device is to be used.

There are numerous ways of achieving a two-step activation of a delivery device. WO2015004048 discloses an example of a device wherein a needle shroud 7 is coupled to a syringe carrier 8 such that a shroud boss 7.1 engages a carrier opening 8.6 to hold the syringe carrier 8 against the force of a spring. At the same time the shroud boss 7.1 is held against a case boss 2.10 to prevent the shroud boss 7.1 from disengaging the carrier opening 8.6. In a first step the needle shroud is pressed against an injection site such that the needle shroud and the syringe carrier are retracted into the case 2. In a second step the needle shroud is further retracted into the housing, whereby the shroud boss 7.1 is freed of the case boss 2.10. The syringe carrier 8 also abuts a rear wall of the case 2, causing the shroud boss to be radially deflected out of the shroud opening 8.6 such that the syringe carrier is released for skin penetration.

The disclosed prior art is complicated in that it requires both the needle shroud and the syringe carrier to move jointly, relative to the case, in a first step. In the second step the case and the syringe carrier move jointly, relative to the needle shroud.

An aim of the present invention is to remedy the drawbacks of prior art and to provide an alternative container holder assembly, wherein the container holder is prevented from moving prior to activation. By means of the present invention, a container holder may be held relative to a housing and be released as a needle guard moves relative to the housing and relative to the container holder.

SUMMARY

An object of the present invention is to provide a medicament delivery device wherein the drawbacks of the state of the art devices are remedied.

In the present application, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

Further, the term "longitudinal", with or without "axis", refers to a direction or an axis through the device or components thereof in the direction of the longest extension of the device or the component.

The term "lateral", with or without "axis", refers to a direction or an axis through the device or components thereof in the direction of the broadest extension of the device or the component.

In a similar manner, the terms "radial" or "transversal", with or without "axis", refers to a direction or an axis through the device or components thereof in a direction generally perpendicular to the longitudinal direction, e.g. "radially outward" would refer to a direction pointing away from the longitudinal axis.

Also, if nothing else is stated, in the following description wherein the mechanical structure of the device and the mechanical interconnection of its components is described, the device is in an initial non-activated or non-operated state.

An embodiment of the present invention relates to a container holder assembly for a medicament delivery device comprising a housing part, fixedly mounted relative to a longitudinally elongated housing, a container holder for accommodating a medicament container, which container holder is longitudinally movable relative to the housing part from a distal, initial position to a proximal, end position, a spring-biased needle guard, coaxial with the container holder and releasably connected with the container holder, and longitudinally movable relative to the housing part between an extended position and a retracted position, wherein the housing part is coaxially arranged between the container holder and the needle guard, and wherein the needle guard is configured to disconnect from the container holder upon movement from the extended position to the retracted position.

In a further aspect, when the container holder is in the initial position, the needle guard is configured to re-connect with the container holder upon movement from the retracted position to the extended position.

In a further aspect, the needle guard is connected with the container holder when the needle guard is in the extended position and the container holder is in the initial position.

In a further aspect, the container holder is prevented from longitudinal movement when the needle guard is connected with the container holder.

In a further aspect, the housing part comprises a longitudinal slit through which the needle guard is connected with the container holder.

In a further aspect, the needle guard is connected with the container holder by a first connecting member of the needle guard radially biasing a resilient second connecting member of the container holder.

In a further aspect, the needle guard is connected to the container holder, the second connecting member is radially biased into engagement with a holding member of the housing part, such that the container holder is prevented from longitudinal movement relative to the housing part.

In a further aspect, the first connecting member is a proximally directed arm and wherein the second connecting member is a distally directed tongue such that distal movement of the needle guard, relative to the container holder, disconnects the first connecting member from the second connecting member.

In a further aspect, the first connecting member is wedge-shaped, the second connecting member comprises a radially outwardly directed protrusion and wherein the holding member is a recess.

In a further aspect, the container holder, in the end position, is prevented from moving proximally relative to the housing part.

In a further aspect, when the needle guard is in the retracted position, movement of the container holder from the initial position to the end position is caused by proximal movement of a spring-biased drive member 30.

In a further aspect, the spring-biased drive member 30 may be released to move proximally by an activation device, when the needle guard is in the retracted position.

In a further aspect, when the container holder is in the end position, the needle guard is configured to move to a locking position upon movement from the retracted position, in which locking position the needle guard is locked relative to the housing part.

In a further aspect, the locking position is proximal of the extended position.

In a further aspect, a latch member locks the needle guard relative to the housing part in the locking position.

In a further aspect, a medicament delivery device comprises a container holder assembly according the invention.

BRIEF DESCRIPTION OF THE DRAWINGS

The figures below disclose an embodiment of the invention for illustrational purposes only. In particular, the disclosure within the figures is not meant to limit the range of protection of the invention. The embodiment shown may be modified in different ways within the scope of the claims.

DETAILED DESCRIPTION

Figure 1:
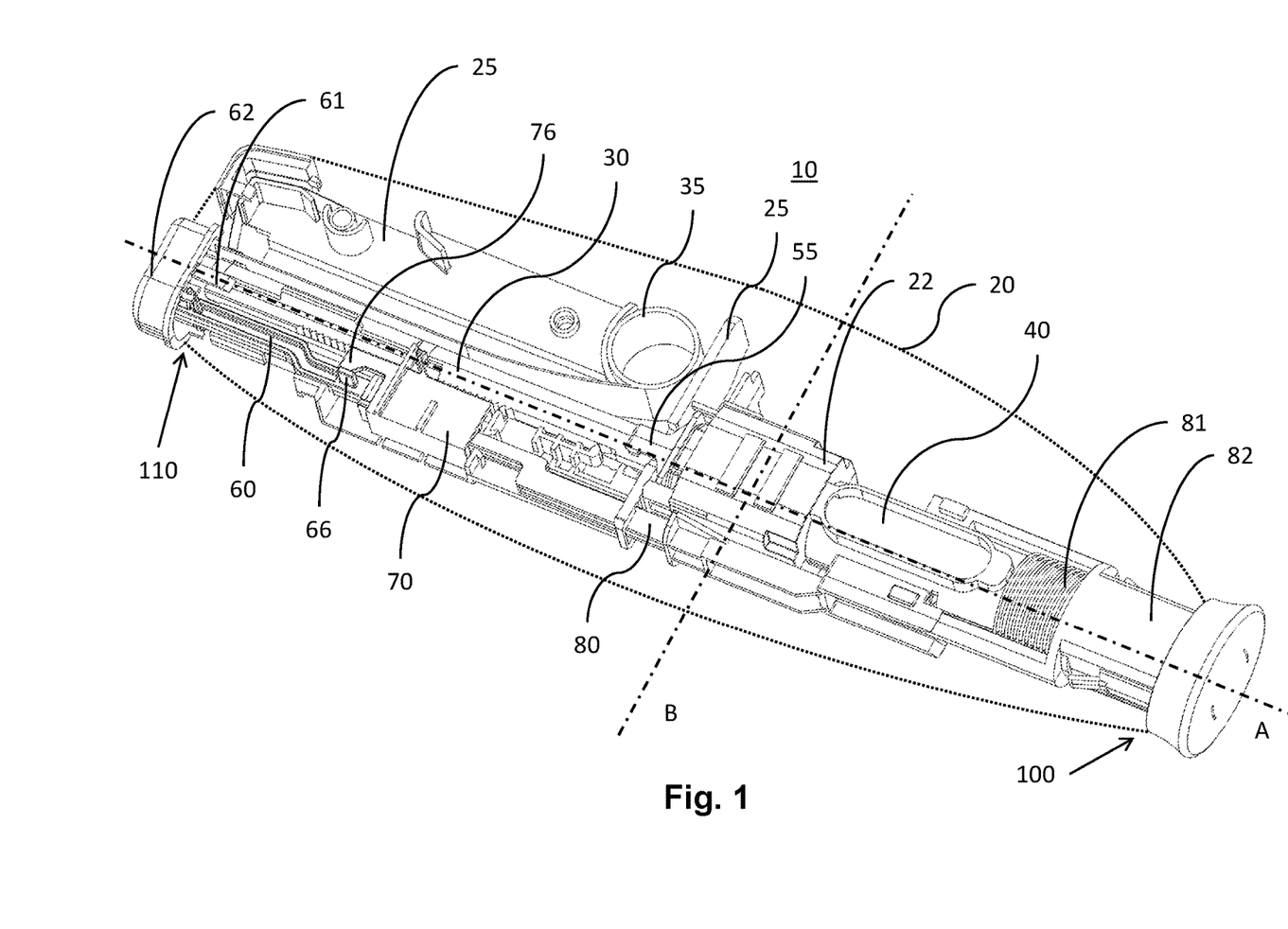
FIG. 1 a perspective view of a medicament delivery device comprising a container holder assembly according to the invention.

FIG. 1 shows a perspective view of a medicament delivery device 10, having a housing 20 elongated along a generally longitudinal axis A, which housing has a proximal end 100 and a distal end 110. The housing 20 disclosed in FIG. 1 is visualized by a dotted line to show the general outline of the housing. A lateral axis B is orthogonal to the longitudinal axis A.

A drive member 30, such as a plunger rod, is configured to be activated to initially exert a force on a container holder retainer 55. When the container holder retainer 55 is released from the drive member, the drive member 30 exerts the force on the stopper (not shown) in a medicament container 40 instead to cause an expulsion of medicament. The medicament container 40 is held in a container holder 50 (FIG. 2), movably accommodated in a housing part 22. The housing part 22 is fixedly attached to the housing 20, or is an integral part of the housing 20. The drive member 30 is force-biased and longitudinally movable relative to the housing 20. When activated, the exerted force initially drives the container holder retainer 55 and the container holder 50 forward to perform a skin penetration, via an injection needle mounted on the housing part 22, or attached directly to the container 40, as is the case if the container 40 is a syringe. Subsequently, the container holder retainer 55 disengages from the drive member 30, whereby the force creates a pressure on a liquid medicament in the medicament container 40 as the plunger rod starts to move in relation to the container, such that the medicament may be expelled through a delivery member 46. The delivery member 46 may be a nozzle, a mouthpiece, a needle (FIG. 2), or similar, for delivering the medicament to an area of treatment on, or in, a patient's body. The force is exerted by an energy accumulating member 35, such as a drive spring. In the embodiment shown, the energy accumulating member 35 is a flat spiral spring, e.g. a clock spring, or a constant force spring, but the force exerted by the drive member could also be realized using a coil spring, a variable force spring or by pressurized fluid or by electrical means. The energy accumulating member 35 could for instance be arranged inside a hollow space in the drive member 30.

The housing 20 may comprise a chassis 25, fixedly attached to the housing, having guide tracks configured to restrict movement of a first activation member 60, a second activation member 80 and a locking unit 70, respectively, to bi-directional movement relative to the chassis 25, and to the housing 20.

The chassis 25 further comprises a drive member guide track configured to restrict movement of the drive member 30 to bidirectional longitudinal movement relative to the chassis, and to the housing.

It should be noted that the chassis 25, shown in the figures, constitutes only a first half of the full chassis. A second half of the chassis is configured to mate with the first half to sandwich the components of the mechanism there between, inside the full chassis.

In another embodiment, the first guide tracks and the drive member guide track are instead configured as integral structures on the inner surface of the housing 20, such that the chassis 25 may be dispensed with. In this way, the number of components may be reduced, which lowers costs and may simplify assembly of the medicament delivery device.

Activation Mechanism

In the following, an example of an activation mechanism will be described. It should however be noted that the present invention may be used together with many kinds of activation mechanisms and is not limited to the herein-described example. Any activation mechanism that releases a drive member to advance the medicament container and to subsequently expel the medicament is usable together with the present invention.

The activation mechanism comprises, apart from the aforementioned drive member 30, the locking unit 70, movable relative to the housing 20, the first activation member 60 movable relative to the housing, and the second activation member 80 movable relative to the housing. The locking unit further comprises a key member (not shown), movable relative to the locking unit 70.

The first activation member 60 and the second activation member 80 comprise a first activation member extension and a second activation member extension, respectively, protruding outside the housing 20 for manual actuation by a user. In the embodiment shown in the figures, the first activation member extension 60 comprises a push button 62 and the second activation member comprises a needle guard 82. However, as readily recognized by a skilled person, the activation mechanism could be turned 180 degrees around a lateral axis so that the first activation member extension would comprise the needle guard, and so that the second activation member extension would comprise the push button. The principle of operation of the activation mechanism would still be the same as described herein.

The locking unit 70 comprises a key member (not shown), movable relative to the locking unit 70 from a neutral position to a cooperating position. The purpose of the key member is to transform a longitudinal force of the first and second activation members 60, 80 into a lateral force which may displace the locking unit, away from the drive member 30.

Initially, the first activation member 60 is in the first initial position and the second activation member 80 is in the second initial position. A user actuates an activation member by exerting a manual force on either the first activation member 60 or on the second activation member 80, which will cause movement of the respective activation member. Resilient elements, or springs, may be arranged to return the activation members to the respective initial positions if the user removes the exerted force. As an example of the embodiment shown in the drawings (FIG. 1), the second activation member extension 82, e.g. a needle guard, may be arranged with a spring 81 and the first activation member extension, e.g. a push button, may be arranged with resilient elements 61. The resilient elements 61 may for instance be arranged in a force-biased interaction with the housing 20 or the chassis 25, so that actuation of the first and the second activation member extensions causes a tensioning of the resilient elements 61 of the first activation member extension 62 and also a tensioning of the spring 81 of the second activation member extension 82, and wherein return movement of the first activation member extension 62 and the second activation member extension 82 is caused by a return movement of the resilient elements 61 and the spring 81, respectively, as they return from a tensioned state to a more relaxed state when the user stops actuating the activation member extensions.

If the first activation member 60 is actuated on its own i.e. no actuation of the second activation member 80, the first activation member 60 will move proximally to the first activation position. If the key member is currently located in the neutral position, the key member will be moved proximally, to the cooperating position, by interaction of the first activation member 60 with a distally directed surface of the key member.

On the other hand, if the key member is already located in the cooperating position, the first activation member 60 will move proximally to the first activation position, in which position the first activation member 60 will be adjacent the distally directed surface of the key member.

In case the second activation member 80 is actuated on its own, i.e. no actuation of the first activation member 60, the second activation member 80 will move distally to the second activation position. If the key member is currently located in the neutral position, the second activation member 80 will move distally to the second activation position, in which position the second activation member 80 will be adjacent a second surface of the key member.

On the other hand, if the key member is currently located in the cooperating position, the key member will be moved distally, to the neutral position, by interaction of the second activation member 80 with the second surface.

In case the first activation member 60 and the second activation member 80 are actuated in combination, the first activation member 60 and the second activation member 80 are moved to the first activation position and to the second activation position, respectively. Due to the actuation of the first activation member 60, i.e. movement and maintained pressure on the first activation member 60, the key member will be moved towards the cooperating position, which is a movement towards the second activation member 80. However, since the second activation member 80 is either already in the second activation position, or moving towards the second activation position, movement of the key member towards the cooperating position, or maintained pressure on the key member in the cooperating position, will cause the second activation member to begin sliding against the second surface of the key member, which second surface is slanted in relation to the longitudinal axis A and to the lateral axis B. Consequently, since the key member is restricted to bi-directional longitudinal movement in relation to the locking unit 70, the combined interaction of the first activation member 60 with the distally directed surface, and the end second activation member 80 with the second surface, will cause a lateral component force between the slanted second surface and the second activation member, which lateral force will be transferred from the key member to the locking unit 70. The lateral force will thus push the locking unit 70 from the locked position to the unlocked position, thereby disengaging the locking unit from the drive member 30, releasing the spring-biased drive member 30 for movement.

In the unlocked position, the spring-biased drive member 30 is released to move proximally and expel the contents of the medicament container 40 of the medicament delivery device 10.

Figure 2:
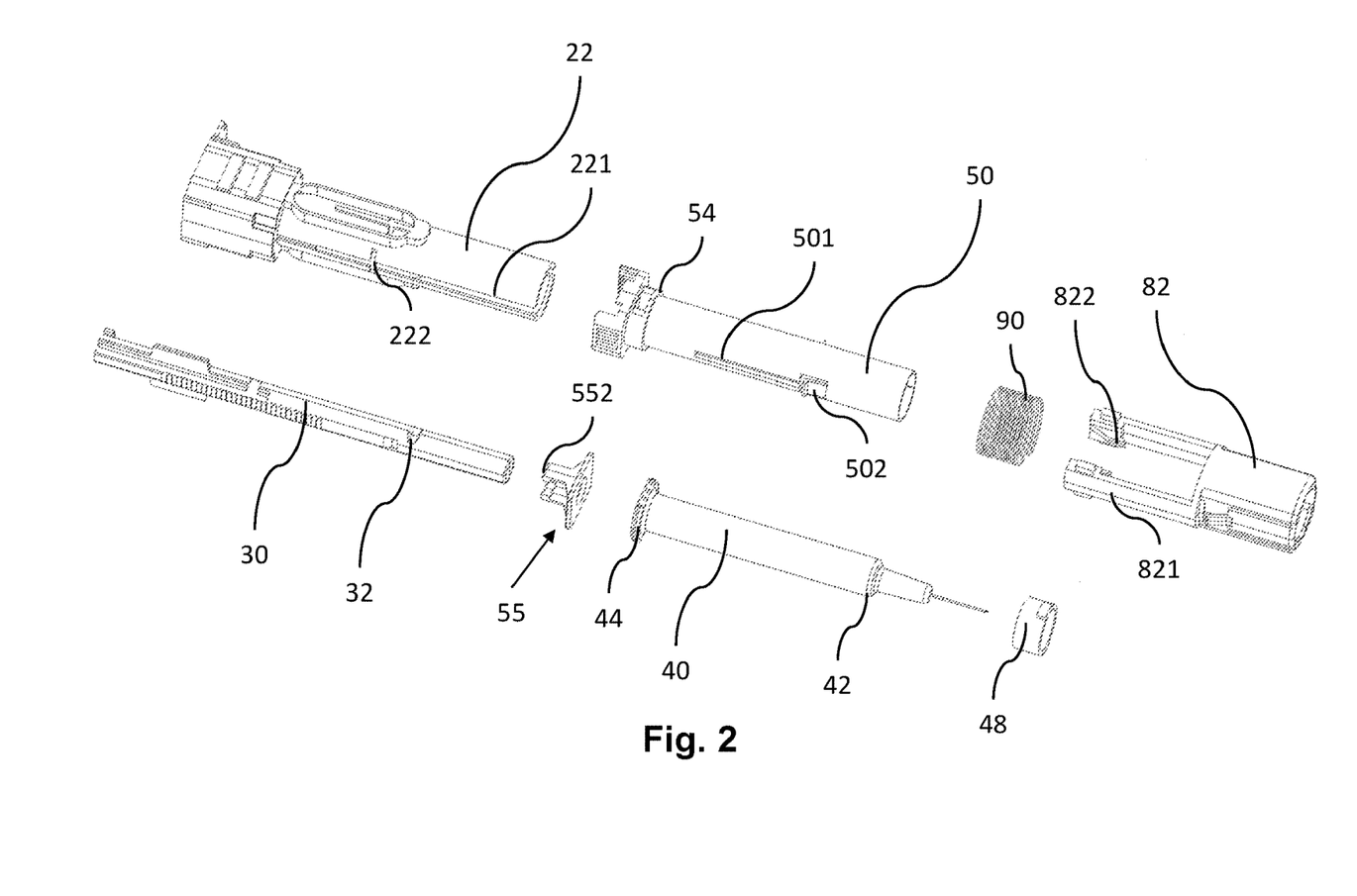
FIG. 2 an exploded perspective view of the container holder assembly, along with additional components FIG. 3-6 side-views of different operational states of the container holder assembly FIG. 7 a cross-sectional view of the container holder assembly in a medicament delivery device

Container Holder Assembly A container holder assembly of the medicament delivery device 10 comprises the housing part 22, the container holder 50, and the needle guard 82 shown in FIG. 2.

The housing part 22 is fixedly mounted relative to the housing 20. Alternatively, the housing part 22 may form an integral, or unitary, part of the housing 20. The housing part 22 is further generally tubular and is coaxially arranged between the container holder 40 and the needle guard 82.

The housing part 22 comprises a first longitudinal slit 221 along a tubular wall of the housing part 22. The first longitudinal slit comprises a holding member 222 in a distal part of the first longitudinal slit 221. The holding member 222 may for instance be a recess, a groove or a transversal slit, the purpose of which will be described in more detail below.

The container holder 50 is longitudinally movable relative to the housing part 22 from a distal, initial position to a proximal, end position. The container holder 50 is generally tubular and is coaxially arranged radially inside the housing part 22. The container holder 50 is configured to accommodate the medicament container 40 therein. The container holder 50 comprises a second longitudinal slit 501 along a tubular wall of the container holder. At a proximal end of the second longitudinal slit 501, a resilient second connecting member 502 is arranged. The second connecting member may be formed as a resilient cut-out of the tubular wall of the container holder 50, e.g. as distally directed resilient tongue. The second connecting member 502 may also comprise a radially outwardly directed protrusion configured to engage with the holding member 222, as will be described below.

The needle guard 82 is spring-biased by a guard spring 90 and is coaxially arranged radially outside the container holder 50 and the housing part 22. The needle guard 82 is longitudinally movable relative to the housing part 22 between an extended position and a retracted position. The needle guard 82 is releasably connected to the container holder 50 when the needle guard 82 is in the extended position. In this regard, the needle guard 82 comprises a first connecting member 822 configured to radially bias the second connecting member 502 of the container holder 50. The bias of the second connecting member 502 forces the second connecting member 502 into engagement with the holding member 222 such that the container holder is held longitudinally fixed, i.e. prevented from longitudinal movement, relative to the housing part 22 in the initial position. The first connecting member 822 is arranged on the distal end of a distally directed arm 821 which extends from a proximal tubular part of the needle guard 82. The first connecting member 822 further protrudes radially inwards and is wedge-shaped in the proximal direction, e.g. hook-shaped, and is configured to be able to bias the second connecting member radially outwards. The outward bias on the second connecting member is achieved by the needle guard spring 90 forcing the needle guard 82 proximally such that the wedge-shaped first connecting member 822 interacts with a distal edge of the second connecting member 502 causing a radially outwardly directed force to act on the resilient second connecting member 502.

Figure 7:
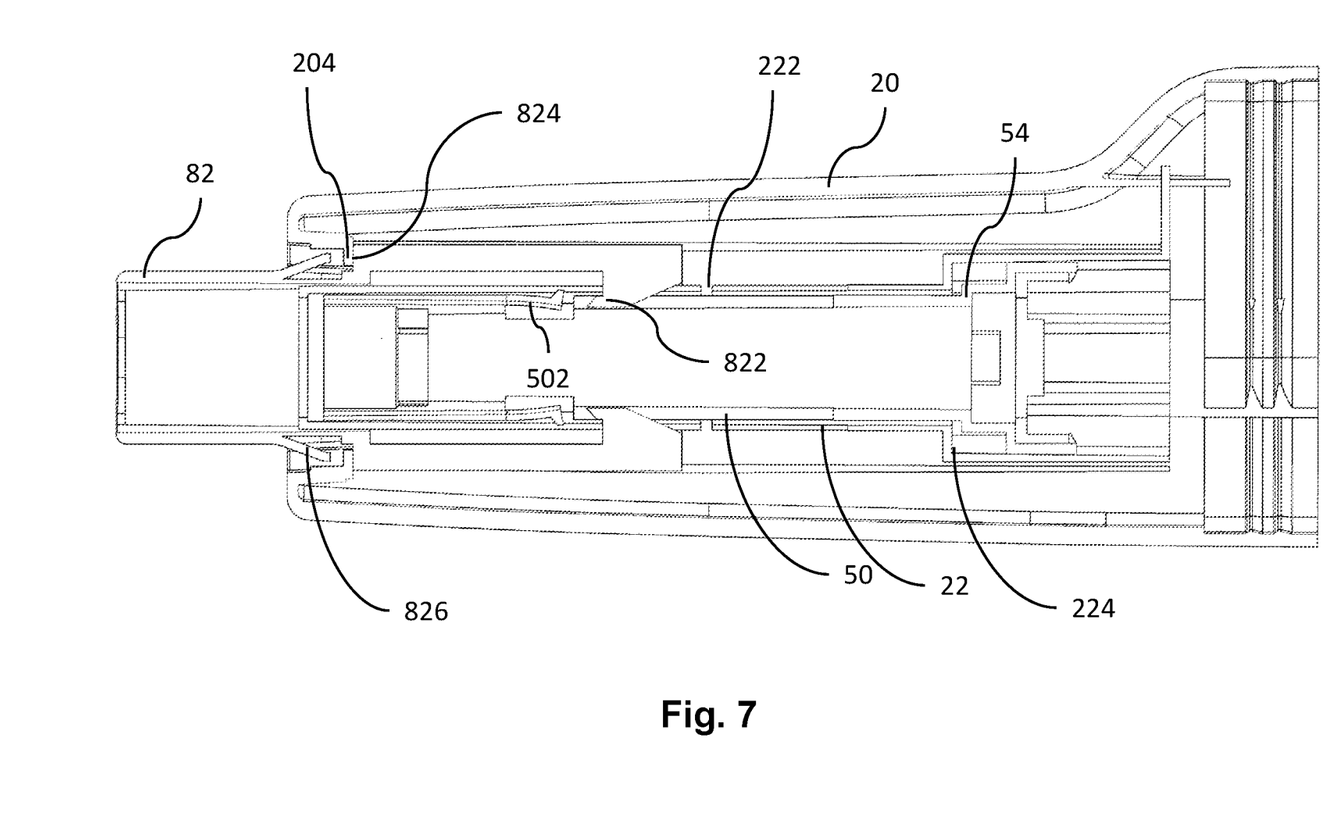

In an assembled state of the container holder assembly, FIG. 7, the first connecting member 822 of the needle guard 82 extends through the slit 221 of the housing part 22 such as to connect with the second connecting member 502 of the container holder 50. Furthermore, when the needle guard 82 is connected to the container holder 50 in the extended position, the needle guard 82 is prevented from moving proximally relative to the container holder 50, under bias of the needle guard spring 90, due to the engagement between the first connecting member 822 and the second connecting member 502.

In FIG. 2 is further illustrated the drive member 30 and a container retainer 55. The drive member 30 is spring-biased, as shown in FIG. 1, and is prevented from moving proximally by the container retainer 55 which is fixedly attached to a distal end of the container holder 50. The container retainer 50 comprises a through-hole, through which the drive member 30 may extend into the container 40. The container retainer 55 is further releasably attached to grooves 32 of the drive member 30 via gripping member 552 of the container retainer 55. As a result, the drive member 30 is releasably attached to the container holder 50 via the container retainer 55.

The container 40 may be a syringe, having a fixed needle, or a cartridge to which a needle has to be attached. The container 40 is accommodated in the container holder 50 and is held fixed relative to the container 40 holder between an internal ledge of the container holder 50, abutting a shoulder 42 of the container, and the container retainer 55, which is fixed to the container holder 50 and abuts a distal flange 44 of the container 40. The container is further arranged with a resilient collar 48 which is positioned between the flange 44 and a distal ledge of the container holder 50, in order absorb forces acting on the container 40, resulting from the pressure of the spring-biased drive member 30.

The function of the container holder assembly will now be described in more detail. FIGS. 3-6 show different states of the container holder assembly during use of the medicament delivery device comprising the assembly. The housing part 22 is depicted separate from the container holder 50 and the needle guard 82 and serves as a position reference since the container holder 50 and the needle guard 82 are movable in relation to the housing part 22. A dashed line D has further been added as a reference for the holding member 222, to show movement of other components relative to the holding member 222.

Figure 3:
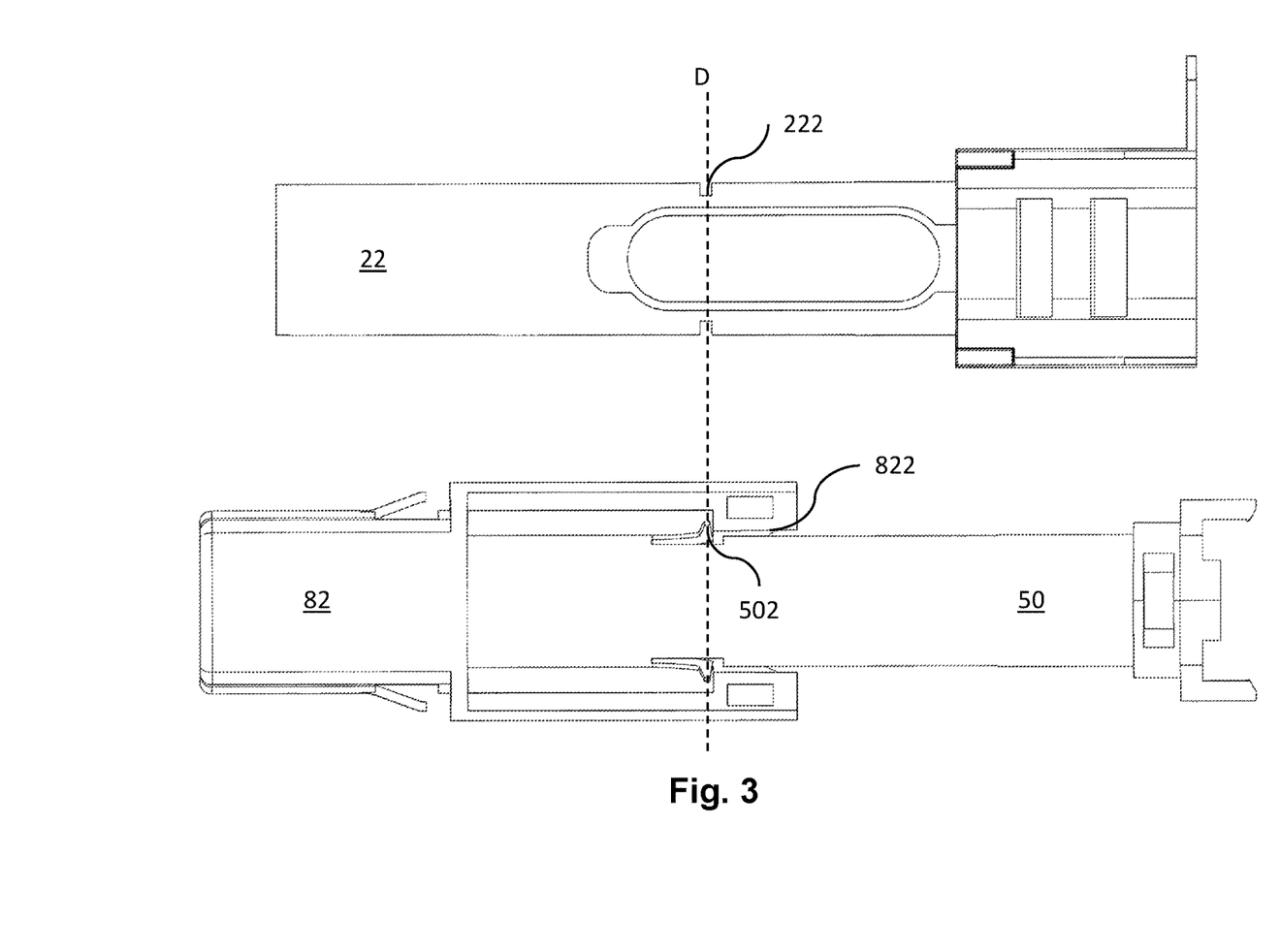

FIG. 3 illustrates an embodiment where the container holder 50 is in the in the initial position and the needle guard 82 is in the extended position. The initial position of the container holder 50 is defined as the position where the second connecting member 502 is aligned with the holding member 222 of the housing part. The extended position of the needle guard 82 is defined as the position where the first connecting member 822 is in engagement with the second connecting member 522 of the container holder 50, and where the container holder is in the initial position. Accordingly, the second connecting member 522 is biased, or flexed, radially outwards by the first connecting member 822, such that the second connecting member engages with the holding member 222 of the housing part 22. The container holder 50 is therefore prevented from longitudinal movement relative to the housing part 22 and the needle guard 82 is prevented from proximal movement relative to the housing part 22.

Figure 4:
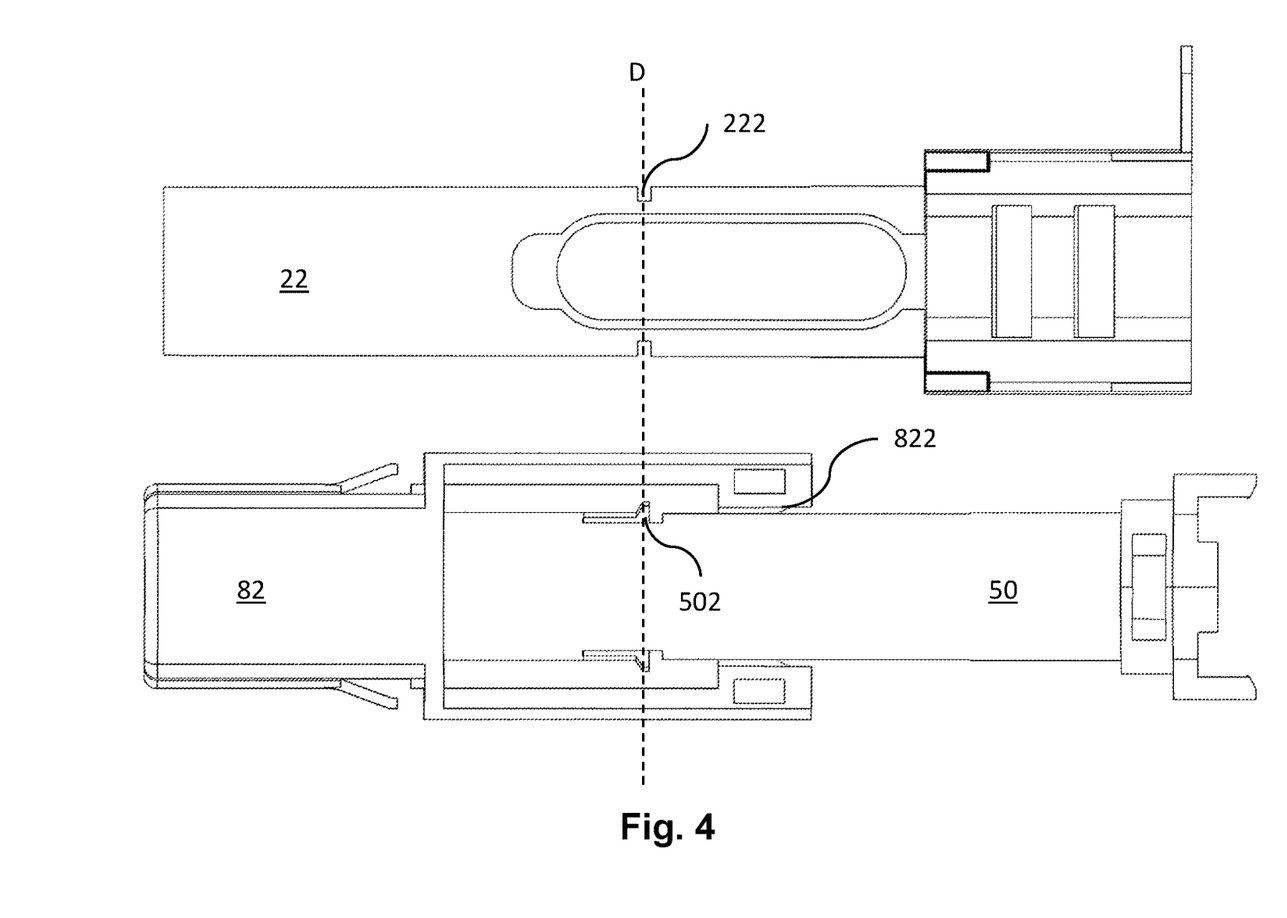

FIG. 4 shows an example where the medicament delivery device comprising the container holder assembly is being activated, for instance by using the activation mechanism described above. In common with many prior art activation mechanisms, the needle guard 82 is pressed against a delivery site against the force of the needle guard spring 90. In FIG. 4 the needle guard 82 is shown in such a state, which is defined as the retracted position of the needle guard 82. The needle guard 82 has been moved distally relative to the housing part 22, resulting in the first connecting member 822 disengaging from the second connecting member 502. The second connecting member is thereby allowed to relax radially inwards such that the holding member 222 is no longer engaged by the second connecting member 502.

Consequently, the container holder 50 is free to move proximally if the drive member 30 should be released by the activation mechanism.

At this stage, if the drive member 30 is not released and the medicament delivery device is removed from the delivery site, the needle guard 82 will make a return movement in the proximal direction, biased by the needle guard spring 90, to the extended position. In the extended position, the needle guard 82 will re-connect with the container holder 50 such that the first connecting member 822 biases the second connecting member 502 radially outwards into engagement with the holding member 222, as shown in FIG. 3. The container holder 50 will once again be prevented from longitudinal movement relative to the housing part 22, and the needle guard 82 will be prevented from further proximal movement relative to the housing part 22.

When the medicament delivery device has been activated by pressing the needle guard 82 against the delivery site, and the drive member 30 has been released under the bias of the energy accumulating member 35, e.g. a drive spring, the force exerted on the drive member is transferred to the container holder 50 via the container retainer 55. Consequently, the container holder 50 is moved from the initial position to the end position by proximal movement of the spring-biased drive member 30, FIG. 5. The drive member 30 pushes the container holder 50 proximally to the end position until the container holder 50 is halted by a proximally facing ledge 54 of the container holder stopping against a distally facing ledge 224 of the housing part 22 (FIG. 7). The position of the container holder 50 where the proximally facing ledge 54 abuts the distally facing ledge 224 of the housing part 22 is defined as the end position of the container holder 50, and is also the position where the delivery member 46 (FIG. 2) of the container 40 has reached a predetermined position for medicament delivery.

Figure 5:
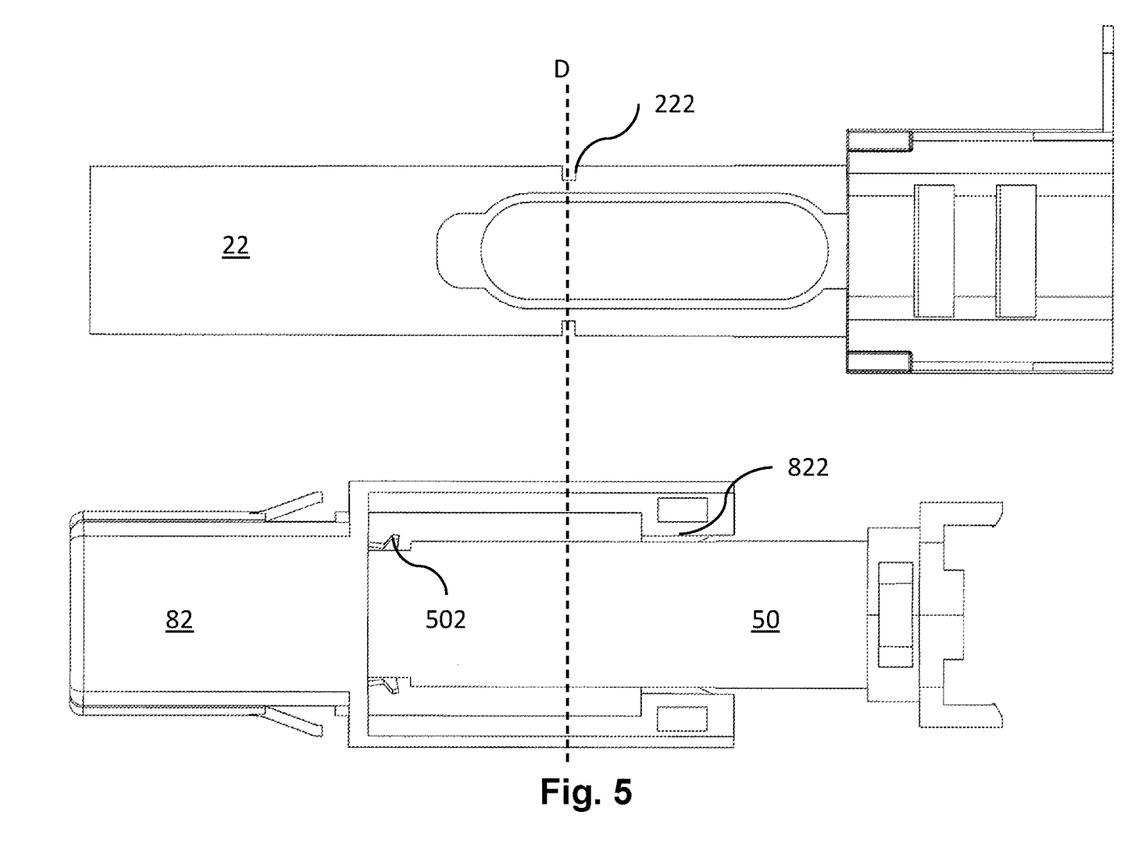
Figure 6:
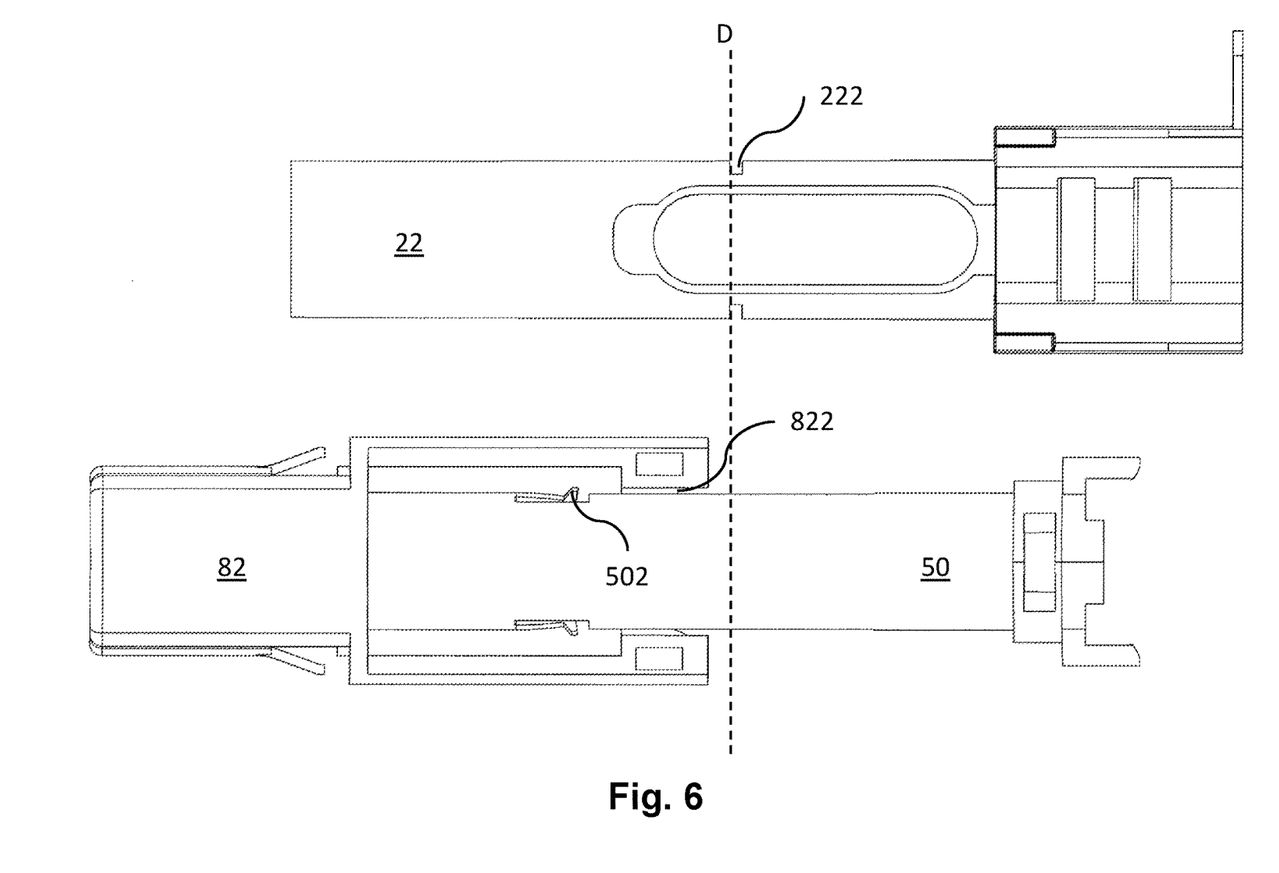

The outwardly directed protrusion of the second connecting member is somewhat slanted with regard to a plane perpendicular to the longitudinal axis A. Therefore, as shown in FIG. 5, when the needle guard 82 is in the retracted position, the first connecting member 822 does not prevent the second connecting member 502 from flexing radially inwards under the bias from the drive member 30, such that the second connecting member 502 disconnects from the holding member 222.

Thereafter, the container holder 50 moves from the initial position to the end position, while the second connecting member 502 slides, in an inwardly deflected state, against the inside surface of the housing part 22.

When the end position is reached, and the container holder 50 is halted by the housing part 22, the force acting between the container retainer 55 and the drive member 30 instantly increases due to the arrest of the drive member 30 and the container holder 50 relative to the housing part 22, such that gripping members 552 of the container retainer 55 are forced out of engagement with the grooves 32 of the drive member 30. As a result the drive member starts to move proximally relative to the container holder 50, thereby expelling the medicament of the container 40 accommodated in the container holder 50.

The use of the container retainer 55 for holding, and for subsequently releasing, the drive member 30 relative to the container holder 50, is generally known in the art.

When the medicament has been completely delivered, the user removes the medicament delivery device form the delivery site. The needle guard 82 then moves proximally under the bias of the needle guard spring 90. Because the container holder 50 is in the end position, the first connecting member 822 of the needle guard 82 does not re-connect with the second connecting member 502 of the container holder 50, but is allowed to travel further proximally, relative to the housing part 22, to a locking position, FIG. 7.

The locking position is proximal of the extended position of the needle guard 82. Proximal movement of the needle guard is halted in the locking position by a proximally-facing surface 824 of the needle guard 82 abutting a stop member 204 of the housing 20. The stop member 204 may be a ledge, a surface, a protrusion, etc.

Furthermore, the needle guard comprises a locking member 828, such as a resilient latch, configured to engage a corresponding locking member of the housing 20. In the described embodiment, the corresponding locking member is the stop member 204. The locking member 828 is proximal of the proximally-facing surface 824. As the needle guard 82 moves proximally, the locking member 828 passes the stop member 204 of the housing 20 such that the locking member 828 engages the stop member 204 before the needle guard 82 comes to a halt in the locking position. The engagement causes the locking member 828 to lock the needle guard 82 relative to the housing part 22, and to the housing 20, in the locking position.

When the needle guard 82 is locked to the housing 20, the medicament delivery device may be safely discarded.

The invention claimed is:

1. Container holder assembly for a medicament delivery device, which container holder assembly comprises;
   a housing part, fixedly mounted relative to a longitudinally elongated housing;
   a container holder for accommodating a medicament container, which container holder is longitudinally movable relative to the housing part from a distal, initial position to a proximal, end position;
   a spring-biased needle guard, coaxial with the container holder and releasably connected with the container holder, and longitudinally movable relative to the housing part between an extended position and a retracted position;
   wherein the housing part is coaxially arranged between the container holder and the needle guard,
   wherein the housing part comprises a first longitudinal slit through which the needle guard is connected with the container holder,
   wherein the needle guard is connected with the container holder by a first connecting member of the needle guard radially biasing a resilient second connecting member of the container holder,
   wherein the needle guard is configured to disconnect from the container holder upon movement from the extended position to the retracted position, and
   wherein, when the needle guard is connected to the container holder, the second connecting member is radially biased into engagement with a holding member of the housing part, such that the container holder is prevented from longitudinal movement relative to the housing part.

2. Container holder assembly for a medicament delivery device according to claim 1, wherein, when the container holder is in the initial position, the needle guard is configured to re-connect with the container holder upon movement from the retracted position to the extended position.

3. Container holder assembly for a medicament delivery device according to claim 1, wherein the needle guard is connected with the container holder when the needle guard is in the extended position and the container holder is in the initial position.

4. Container holder assembly for a medicament delivery device according to claim 3, wherein the container holder is prevented from longitudinal movement relative to the housing part when the needle guard is connected with the container holder.

5. Container holder assembly for a medicament delivery device according to claim 1, wherein the first connecting member is a proximally directed arm and wherein the second connecting member is a distally directed resilient tongue such that distal movement of the needle guard, relative to the container holder, disconnects the first connecting member from the second connecting member.

6. Container holder assembly for a medicament delivery device according to claim 5, wherein the first connecting member protrudes radially inward and is wedge-shaped, the second connecting member comprises a radially outwardly directed protrusion and wherein the holding member is a recess.

7. Container holder assembly for a medicament delivery device according to claim 1, wherein the container holder, in the end position, is prevented from moving proximally relative to the housing part.

8. Container holder assembly for a medicament delivery device according to claim 1, wherein the container holder assembly further comprises a spring-biased drive member, and when the needle guard is in the retracted position, movement of the container holder from the initial position to the end position is caused by proximal movement of the spring-biased drive member.

9. Container holder assembly for a medicament delivery device according to claim 8, wherein the spring-biased drive member may be released to move proximally by an activation device, when the needle guard is in the retracted position.

10. Container holder assembly for a medicament delivery device according to claim 1, wherein, when the container holder is in the end position, the spring-biased needle guard is configured to move to a locking position upon movement from the retracted position, in which locking position the needle guard is locked relative to the housing part.

11. Container holder assembly for a medicament delivery device according to claim 10, wherein the locking position is proximal of the extended position.

12. Container holder assembly for a medicament delivery device according to claim 11, wherein a locking member locks the needle guard relative to the housing part in the locking position.

13. Container holder assembly for a medicament delivery device according to claim 10, wherein the locking position is proximal of the extended position.

14. Medicament delivery device comprising a container holder assembly according to claim 1.

15. Container holder assembly for a medicament delivery device according to claim 1, wherein the needle guard is connected with the container holder when the needle guard is in the extended position and the container holder is in the initial position.

16. Container holder assembly for a medicament delivery device according to claim 15, wherein the container holder is prevented from longitudinal movement relative to the housing part when the needle guard is connected with the container holder.

17. Container holder assembly for a medicament delivery device, which container holder assembly comprises;
  a housing part, fixedly mounted relative to a longitudinally elongated housing;
  a container holder for accommodating a medicament container, which container holder is longitudinally movable relative to the housing part from a distal, initial position to a proximal, end position;
  a spring-biased needle guard, coaxial with the container holder and releasably connected with the container holder, and longitudinally movable relative to the housing part between an extended position and a retracted position;
  wherein the housing part is coaxially arranged between the container holder and the needle guard,
  wherein the housing part comprises a first longitudinal slit through which the needle guard is connected with the container holder,
  wherein the needle guard is connected with the container holder by a first connecting member of the needle guard radially biasing a resilient second connecting member of the container holder,
  wherein the first connecting member is a proximally directed arm and wherein the second connecting member is a distally directed resilient tongue such that distal movement of the needle guard, relative to the container holder, disconnects the first connecting member from the second connecting member, and
  wherein the needle guard is configured to disconnect from the container holder upon movement from the extended position to the retracted position.

18. Container holder assembly for a medicament delivery device according to claim 17, wherein the first connecting member protrudes radially inward and is wedge-shaped, the second connecting member comprises a radially outwardly directed protrusion.

19. Container holder assembly for a medicament delivery device according to claim 17, wherein, when the container holder is in the initial position, the needle guard is configured to re-connect with the container holder upon movement from the retracted position to the extended position.

20. Container holder assembly for a medicament delivery device according to claim 17, wherein the container holder, in the end position, is prevented from moving proximally relative to the housing part.

21. Container holder assembly for a medicament delivery device according to claim 17, wherein, when the container holder is in the end position, the spring-biased needle guard is configured to move to a locking position upon movement from the retracted position, in which locking position the needle guard is locked relative to the housing part.

* * * * *